(12) United States Patent
Kogure et al.

(10) Patent No.: US 11,647,945 B2
(45) Date of Patent: May 16, 2023

(54) EVALUATING APPARATUS AND NON-TRANSITORY COMPUTER READABLE MEDIUM STORING PROGRAM

(71) Applicant: PARAMOUNT BED CO., LTD., Tokyo (JP)

(72) Inventors: Takamasa Kogure, Tokyo (JP); Tomoko Inoue, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 425 days.

(21) Appl. No.: 16/197,743

(22) Filed: Nov. 21, 2018

(65) Prior Publication Data

US 2019/0175103 A1 Jun. 13, 2019

(30) Foreign Application Priority Data

Dec. 7, 2017 (JP) .............................. JP2017-235409

(51) Int. Cl.
*A61B 5/00* (2006.01)
*A61B 5/11* (2006.01)

(52) U.S. Cl.
CPC .......... *A61B 5/4809* (2013.01); *A61B 5/4812* (2013.01); *A61B 5/6892* (2013.01); *A61B 5/1113* (2013.01); *A61B 5/1115* (2013.01); *A61B 5/1118* (2013.01); *A61B 5/7278* (2013.01); *A61B 5/7282* (2013.01)

(58) Field of Classification Search
None
See application file for complete search history.

(56) References Cited

U.S. PATENT DOCUMENTS 9,420,973 B1 8/2016 Konchitsky
2005/0209512 A1* 9/2005 Heruth .................... G16H 20/30
600/587

(Continued)

FOREIGN PATENT DOCUMENTS

JP H05-095914 A 4/1993
JP 2001-061797 A 3/2001

(Continued)

OTHER PUBLICATIONS

Kushida, et al., "Comparison of actigraphic, polysomnographic, and subjective assessment of sleep parameters in sleep-disordered patients," Sep. 2001, Sleep Medicine, vol. 2, Issue 5, pp. 389-396 (Year: 2001).*

(Continued)

*Primary Examiner* — Alex M Valvis
*Assistant Examiner* — Aurelie H Tu
(74) *Attorney, Agent, or Firm* — Wenderoth, Lind & Ponack, L.L.P.

(57) ABSTRACT

An evaluating apparatus of this application includes a detector configured to detect a biological signal of a user, and a controller configured to calculate an amount of activity of the user from the biological signal, determine whether the user is sleeping during a first period by comparing the amount of activity with a low threshold, and determine whether the user is sleeping during a second period after the first period by comparing the amount of activity with a high threshold, the low threshold being lower than the high threshold.

10 Claims, 12 Drawing Sheets

(56) References Cited

U.S. PATENT DOCUMENTS

| | | | |
|---|---|---|---|
| 2005/0234314 A1* | 10/2005 | Suzuki | A61B 5/02438 600/301 |
| 2008/0033304 A1 | 2/2008 | Dalal et al. | |
| 2010/0030118 A1* | 2/2010 | Hiei | A61B 5/4809 600/595 |
| 2013/0226010 A1* | 8/2013 | Hotta | A61B 5/0205 600/483 |
| 2014/0266787 A1* | 9/2014 | Tran | A61B 5/021 340/870.07 |
| 2015/0164238 A1* | 6/2015 | Benson | A61B 5/01 340/540 |
| 2017/0094046 A1* | 3/2017 | Raymann | G08B 21/06 |

FOREIGN PATENT DOCUMENTS

| | | |
|---|---|---|
| JP | 2014-233487 | 12/2014 |
| JP | 2015-150034 A | 8/2015 |
| JP | 2016-067811 A | 5/2016 |

OTHER PUBLICATIONS

Kushida et al., "Comparison of actigraphic, polysmonographic, and subjective assessment of sleep parameters in sleep-disordered patients," 2001, Elsevier, Sleep Medicine 2, 389-396 (Year: 2001).*

* cited by examiner

FIG. 3

| PARAMETER | VALUE |
|---|---|
| SLEEP DETERMINATION THRESHOLD | 1.0 |
| SLEEP ONSET DETERMINATION TIME PERIOD | 6 MINUTES |
| SECOND SLEEP ONSET DETERMINATION TIME PERIOD | 20 MINUTES |
| WAKEFULNESS DETERMINATION TIME PERIOD | 6 MINUTES |

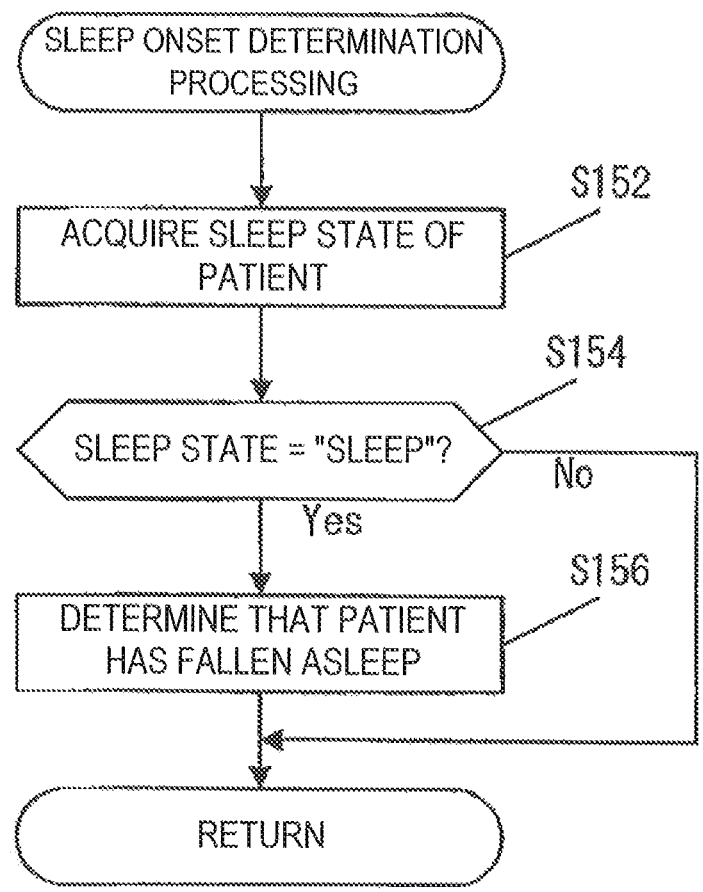

EVALUATING APPARATUS AND NON-TRANSITORY COMPUTER READABLE MEDIUM STORING PROGRAM

CROSS-REFERENCE TO RELATED APPLICATIONS

This application is based upon and claims the benefit of priority from prior Japanese Patent Application No. 2017-235409, filed Dec. 7, 2017, the entire contents of which are incorporated herein by reference.

FIELD

The present embodiment relates to an evaluating apparatus and a non-transitory computer readable medium storing a program.

BACKGROUND

Conventionally, there are various known methods for determining whether a person is in a sleeping state or an awake state.

BRIEF DESCRIPTION OF THE DRAWINGS

FIG. 3 is a diagram for explaining parameters in the first embodiment;

FIG. 6 is a flowchart for explaining processing whether the target person starts falling asleep or not in the first embodiment;

DETAILED DESCRIPTION

Figure 1:
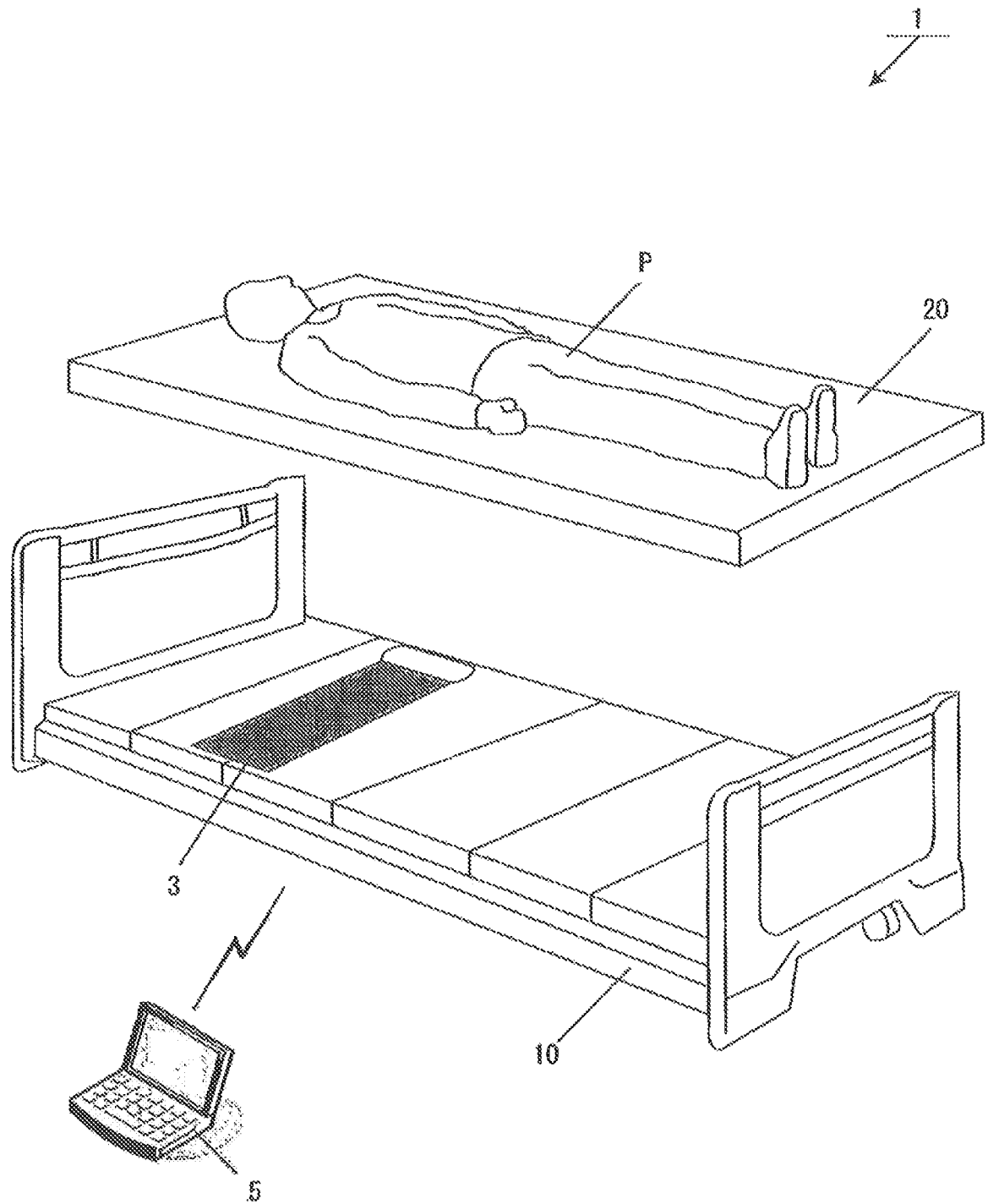
FIG. 1 is a diagram for explaining the evaluating system in a first embodiment.

In general, one aspect of the present application is an evaluating apparatus including a detector configured to detect a biological signal of a user; and a controller configured to: calculate an amount of activity of the user from the biological signal, determine whether the user is sleeping during a first period by comparing the amount of activity with a low threshold, and determine whether the user is sleeping during a second period after the first period by comparing the amount of activity with a high threshold (the high threshold is set in accordance with a determination condition), the low threshold being lower than the high threshold. High and low mean with respect to each other. The apparatus can include a further detector configured to detect physically presence of the user in a bed or to detect that the user is in a recumbent position, wherein the controller begins the first period upon positive detection by the further detector, and upon a determination during the first period that the user is sleeping, the controller ends the first period and begins the second period.

Furthermore, the controller can also end the first period and begin the second period when, during the first period it has not been determined that the user has fallen asleep for a determination time period. The controller can also determine, during the second period, whether the user is awake for a duration, and end second period upon a determination that the user has been awake for the duration.

The controller restarts the first period upon ending the second period and again determines whether the user is sleeping by comparing the amount of activity with the low threshold.

The controller determines that the user has fallen asleep when the calculated amount of activity is continuously substantially 0 for a third time period.

After the first period, in a case where a time period during which it has not been determined that the subject has fallen asleep continues for a predetermined determination time period, the controller determines whether the user is sleeping by comparing the amount of activity with a middle threshold which is greater than the low threshold and which is smaller than the high.

Another aspect of the application is an evaluating apparatus includes a detector configured to detect a biological signal of a user, a controller configured to calculate an amount of activity of the user from the biological signal, calculate a first value from the amount of activity of the user, determine a state of the user as awake if the first value exceeds a first threshold and a magnitude of the biological signal is greater than or equal to a first amount, determine the state of the user as sleeping if the first value is equal to or less than the first threshold and the magnitude of the biological signal is greater than or equal to the first amount, determine the state of the user as awake if the first value exceeds a second threshold, which is smaller than the first threshold, and a magnitude of the biological signal is less than the first amount, and determine the state of the user as sleeping if the first value is equal to or less than the second threshold and the magnitude of the biological signal is less than the first amount.

Another aspect of the application is a non-transitory computer readable medium having stored thereon a program for causing a microprocessor to execute at least the following, acquiring a biological signal of a user, calculating an amount of activity of the user from the biological signal, determining whether the user is sleeping during a first period by comparing the amount of activity with a low threshold, and determining whether the user is sleeping during a second period after the first period by comparing the amount of activity with a high threshold, the low threshold being lower than the high threshold.

One or more embodiments are now described with reference to the drawings, wherein like reference numerals are used to refer to like elements throughout. In the following description, for purposes of explanation, numerous specific details are set forth in order to provide a thorough understanding of the various embodiments. It is evident, however, that the various embodiments can be practiced without these specific details (and without applying to any particular networked environment or standard).

As used in this disclosure, in some embodiments, the terms "component," "system" and the like are intended to refer to, or comprise, a computer-related entity or an entity related to an operational apparatus with one or more specific functionalities, wherein the entity can be either hardware, a combination of hardware and software, software, or software in execution. As an example, a component may be, but is not limited to being, a process running on a processor, a processor, an object, an executable, a thread of execution, computer-executable instructions, a program, and/or a computer. By way of illustration and not limitation, both an application running on a server and the server can be a component.

One or more components may reside within a process and/or thread of execution and a component may be localized on one computer and/or distributed between two or more computers. In addition, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software application or firmware application executed by a processor, wherein the processor can be internal or external to the apparatus and executes at least a part of the software or firmware application. As yet another example, a component can be an apparatus that provides specific functionality through electronic components without mechanical parts, the electronic components can comprise a processor therein to execute software or firmware that confers at least in part the functionality of the electronic components. While various components have been illustrated as separate components, it will be appreciated that multiple components can be implemented as a single component, or a single component can be implemented as multiple components, without departing from example embodiments. Further, the various embodiments can be implemented as a method, apparatus or article of manufacture using standard programming and/or engineering techniques to produce software, firmware, hardware or any combination thereof to control a computer to implement the disclosed subject matter. The term "article of manufacture" as used herein is intended to encompass a computer program accessible from any computer-readable (or machine-readable) device or computer-readable (or machine-readable) storage/communications media. For example, computer readable storage media can comprise, but are not limited to, magnetic storage devices (e.g., hard disk, floppy disk, magnetic strips), optical disks (e.g., compact disk (CD), digital versatile disk (DVD)), smart cards, and flash memory devices (e.g., card, stick, key drive). Of course, those skilled in the art will recognize many modifications can be made to this configuration without departing from the scope or spirit of the various embodiments.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word example or exemplary is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Embodiments described herein can be exploited in substantially any wireless communication technology, comprising, but not limited to, wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), third generation partnership project 2 (3GPP2) ultra mobile broadband (UMB), high speed packet access (HSPA), Z-Wave, Zigbee and other 802.XX wireless technologies and/or legacy telecommunication technologies.

1. First Embodiment 1.1. The Evaluating System

As illustrated in FIG. 1, the system 1 includes a detector 3 placed between a bed 10 and a mattress 20, and a processor 5 for processing some algorithm based on values output from the detector 3. The detector 3 and the processor 5 constitute a system which can output biological information and which evaluates states of the target person.

If the target person (hereinafter, referred to as a "patient P" as an example) is on the mattress 20, the detector 3 detects vibration (vibration produced from a human body) from a biological signal of the patient P. Then, biological information of the patient P is calculated on the basis of the detected vibration. In the present embodiment, it is possible to output and display the calculated biological information (for example, a respiration rate, a heart rate and an amount of activity). Note that the system may be integrally formed by a storage unit (i.e., a non-transitory electronic memory), a display, and the detector 3. Further, because the processor 5 may be a general-purpose apparatus, the processor 5 is not limited to an information processing apparatus such as a computer and may be configured with an apparatus such as, for example, a tablet and a smartphone.

Further, the target person may be an ailing person or a person who needs care. Further, the target person may be a healthy person who does not need care, an elderly person, a child, a disabled person or an animal which is not a person.

Here, the detector 3 is made in a sheet shape. Even if the detector 3 is placed between the bed 10 and the mattress 20, because the detector 3 can be used without providing a feeling of strangeness (i.e., physical discomfort) to the patient P, it is possible to measure a biological information in bed for a long period. That is, biological information, or the like, is acquired as a state of the patient P when the patient P is lying on the bed.

Further, it is possible to determine a position or a posture of the patient P on a bed 10 with the detector 3. For example, it is possible to determine whether a posture of the patient P on the mattress 20 is a recumbent position or a seated position, or it is possible to determine at which position on the mattress 20 the patient is sleeping or in which direction the patient faces.

The detector 3 only has to be able to acquire a biological signal (such as body motion, respiratory movement and ballistocardiogram) of the patient P. In the present embodiment, while a heart rate and a respiration rate can be calculated on the basis of body vibration, it is, for example, also possible to obtain the biological signal of the patient P using an infrared sensor, an acquired video, or the like, or utilizing an actuator with strain gauge. Further, the detector 3 may be implemented by, for example, a smartphone, a tablet, or the like, placed on the bed 10 with a built-in acceleration sensor, or the like.

1.2. Configuration

Figure 4:
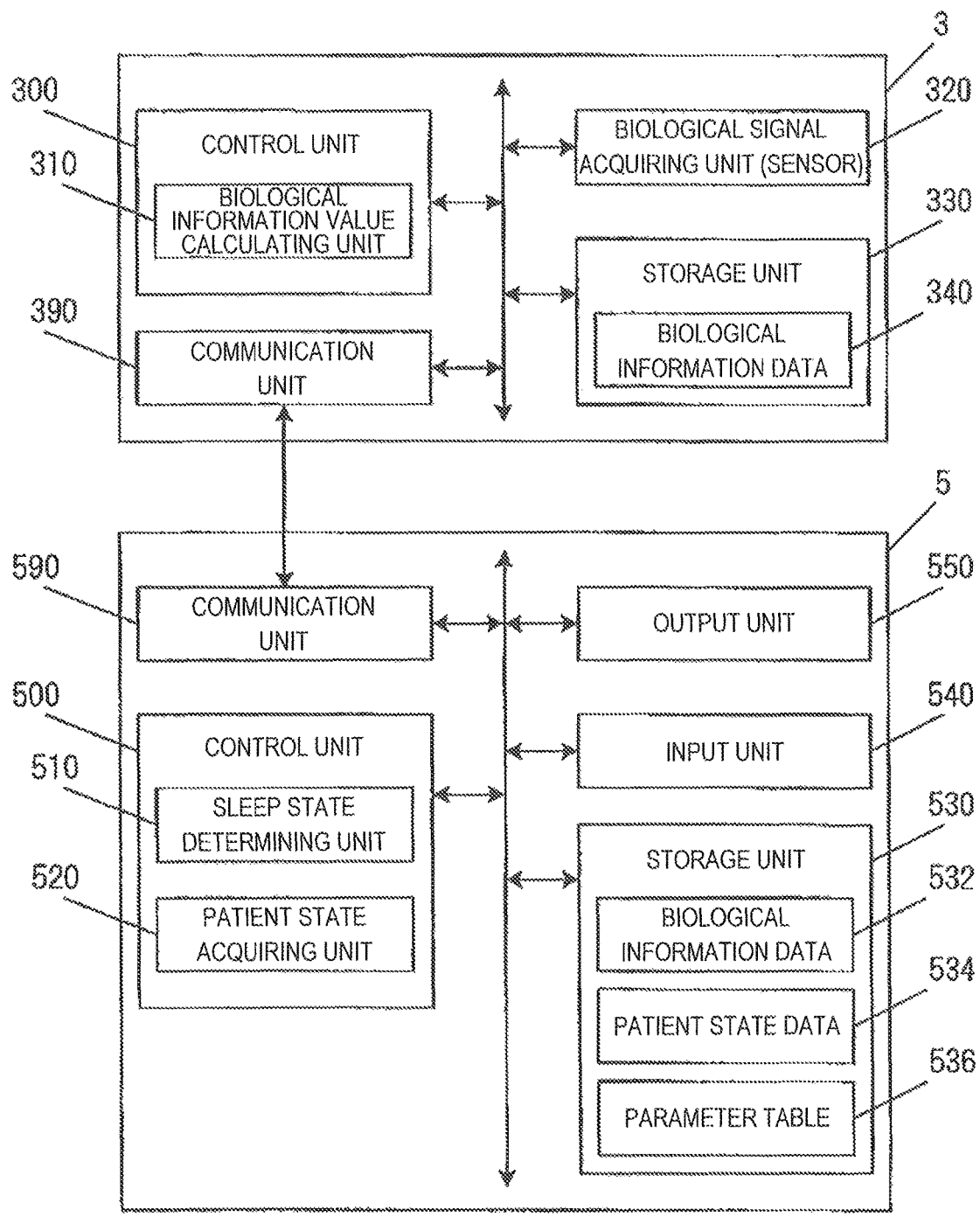
FIG. 4 is a diagram for explaining a configuration of the evaluating system in view of another aspect in the first embodiment.

Subsequently, a configuration of the system 1 will be described with reference to FIG. 2 to FIG. 4. The system 1 includes the detector 3 and the processor 5, and each functional unit other than the biological signal acquiring unit 110 may be implemented by either one of the detector 3 and the processor 5.

Figure 2:
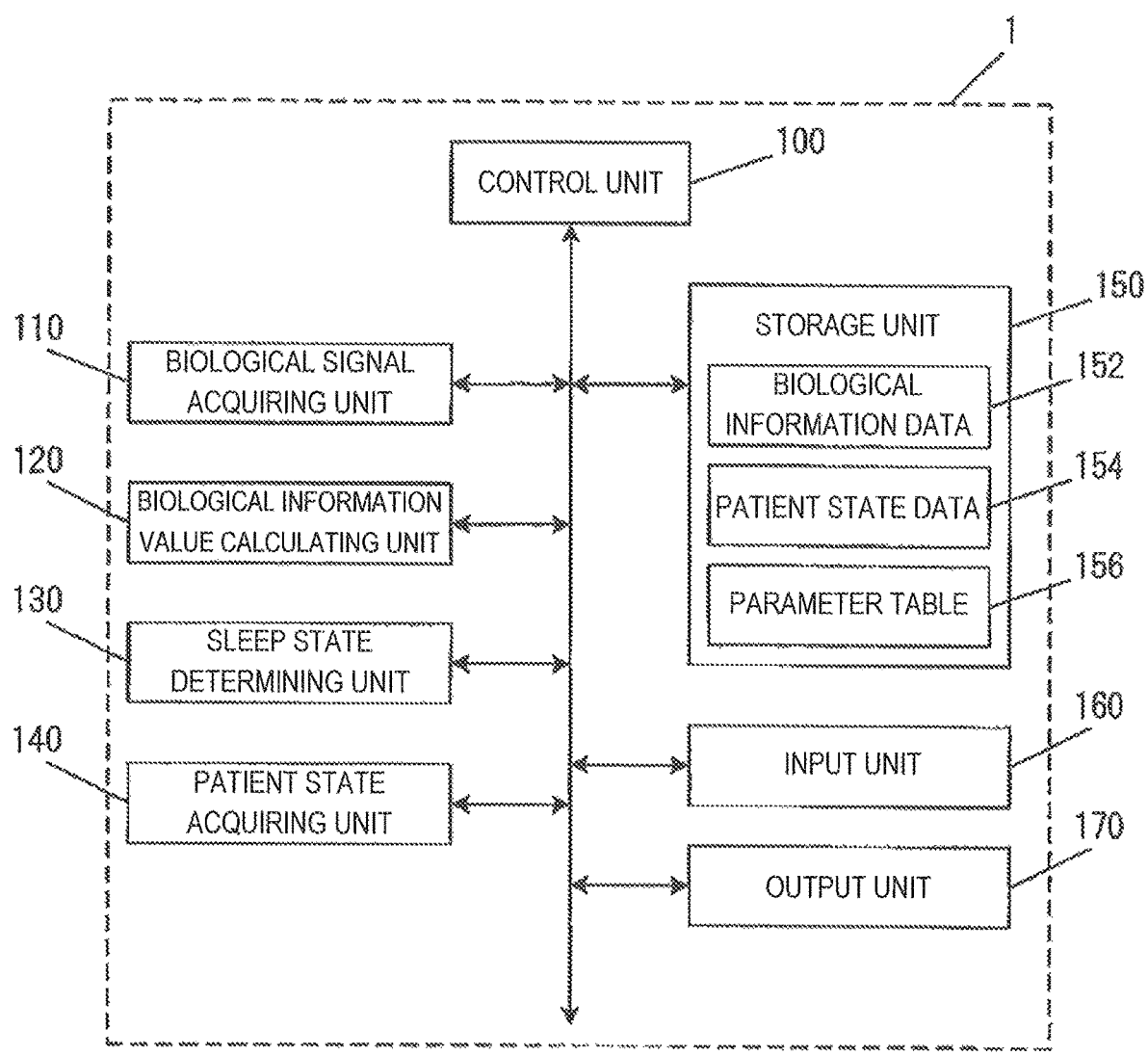
FIG. 2 is a diagram for explaining a configuration of the evaluating system in the first embodiment.

As illustrated in FIG. 2, The system 1 includes a control unit 100, a biological signal acquiring unit 110, a calculating unit 120, a determining unit 130, a patient state acquiring unit 140, a storage unit 150, an input unit 160 and an output unit 170.

The control unit 100 controls operation of the entire system 1. The control unit 100 corresponds to, for example, a control apparatus such as a CPU (Central Processing Unit). The control unit 100 performs various kinds of processing by reading out and executing various kinds of programs stored in the storage unit 150 (which corresponds to, for example, a non-transitory electronic memory apparatus).

While, in the present embodiment, the control unit 100 operates for the whole system, as will be described later in FIG. 4, the control unit 100 can be respectively provided at the detector 3 and/or the processor 5.

The biological signal acquiring unit 110 acquires a biological signal of the patient P. In the present embodiment, as an example, the biological signal acquiring unit 110 comprises a sensor apparatus which detects pressure changes, and with which body vibration, which is one type of the biological signal, is. The acquired biological signal is processed respectively at the calculating unit 120, the determining unit 130 and the patient state acquiring unit 140.

Further, the biological signal acquiring unit 110 may, for example, comprise a pressure sensor which acquires body vibration of the patient, or a load sensor which acquires a changed biological signal based on a changed position which is center of gravity of the patient. Further, the biological signal acquiring unit 110 may, for example, comprise a microphone, e.g., in place of the pressure sensor, to acquire a biological signal on the basis of sound picked up by the microphone. Still further, the biological signal acquiring unit 110 may, for example, comprise a microwave, a laser speckle sensor, or the like, to acquire a biological signal on the basis of displacement of a body of the patient P or bedclothes. Further, the biological signal acquiring unit 110 may, for example, comprise an acceleration sensor or a gravity sensor to acquire a biological signal. In this manner, it is only necessary that a biological signal can be acquired using one of the methods.

The calculating unit 120 calculates a biological information of the patient P. In the present embodiment, it is also possible to extract a respiratory component and a heartbeat component from the body motion (body vibration) acquired by the biological signal acquiring unit 110 and obtain a respiration rate and a heart rate on the basis of a respiratory interval and an R-R interval. Further, it is also possible to analyze periodicity of the body motion and calculate a respiration rate and a heart rate from a peak frequency. Further, the calculating unit 120 functions as an activity amount calculating unit in the case where an amount of activity is calculated as the biological information.

The determining unit 130 is a functional unit for determining a state of the patient. For example, a state of the patient is determined on the basis of the biological signal acquired by the biological signal acquiring unit 110. The state may be determined as an "awake" state or a "sleeping" state, or further, the "sleeping" state may be determined as a "REM sleeping" state or a "non-REM sleeping" state. That is, the state may indicate a depth of sleeping. If "REM sleeping" state may be divided into a plurality of states like a first "REM sleeping" state and a second "REM sleeping" state, the "sleeping" state may include the first "REM sleeping" state and the second "REM sleeping" state. If "non-REM sleeping" state may be divided into a plurality of states like a first "non-REM sleeping" state and a second "non-REM sleeping" state, the "sleeping" state may include the plurality of states like a first "non-REM sleeping" state and a second "non-REM sleeping" state. Further, it is also possible to determine the state of the patient P from combination of the biological information calculated at the calculating unit 120 and change of the biological signal.

The patient state acquiring unit 140 acquires a state of the patient P. For example, the state of the patient P which indicates whether the patient P is in the bed 10 is acquired from the biological signal acquired by the biological signal acquiring unit 110, a load sensor, or the like, separately provided at the bed 10.

Further, it is also possible to acquire a state of the patient P which indicates postures of the patient P (e.g. whether or not the patient P is lying down, is sitting on the mattress 20, sitting on the edge of the mattress 20 or the like) on the basis of the biological signal (for example, body vibration data) acquired by the biological signal acquiring unit 110.

Further, while, in the present embodiment, the state of the patient P which indicates whether the patient P is in the bed 10 is acquired at the patient state acquiring unit 140, that state may be determined also by the determining unit 130.

The storage unit 150 stores various kinds of data and programs for operation of the system 1. The control unit 100 implements various kinds of functions by reading out and executing the programs stored in the storage unit 150. Here, the storage unit 150 is configured with a semiconductor memory (for example, an SSD (Solid State Drive), an SD card (registered trademark)), a magnetic disk apparatus (for example, an HDD (Hard Disk Drive)), or the like. Further, the storage unit 150 may be a built-in storage apparatus or a detachable external storage apparatus. Further, the storage unit 150 may be a storage area of an electronic non-transitory memory of an external server serving as cloud storage.

The storage unit 150 stores biological information data 152, patient state data 154 and a parameter table 156.

The biological information data 152 is the biological information calculated by the calculating unit 120 on the basis of the biological signal (body motion) acquired by the biological signal acquiring unit 110. Note that, in the present embodiment, the storage unit 150 may store a respiration rate, a heart rate, an amount of activity and body motion as necessary. Further, the storage unit 150 may store other information (for example, a respiratory problem index based on fluctuation in a respiratory amplitude, or the like, a periodic body motion index based on periodicity of the body motion) if the information is a biological information which can be calculated by the calculating unit 120.

The patient state data 154 is a state of the patient P. As the state of the patient P, the storage unit 150 stores the state whether the patient P is "sleeping" or "awake" determined by the determining unit 130, or state whether the patient P is in the bed 10 acquired by the patient state acquiring unit 140. Further, the storage unit 150 may also store information indicating the depth of sleeping such as the "REM sleeping" state and the "non-REM sleeping" state, and the storage unit 150 may also store states of postures or positions of the patient P such as "sitting" and a "lateral position" on the mattress 20.

The parameter table 156 is a table in which various kinds of parameters are stored. In the present embodiment, as illustrated in FIG. 3, a threshold for determining the state of the patient (for example, "1.0"), a first time period for determining whether the patient falls asleep (for example, "6 minutes"), a second time period for determining whether the patient falls asleep (for example, "20 minutes") and a time period for determining whether the patient wakes up (for example, "6 minutes") are stored in the storage unit 150. Each parameter will be described in processing which will be described later.

Among the above-described components, the calculating unit 120, the determining unit 130, and the patient state acquiring unit 140 may be implemented by software. For example, the control unit 100 implements each function by reading out and executing software (programs) stored in the storage unit 150. That is, the control unit 100 functions as each component by software being executed.

Further, the control unit 100 functions as the determining unit 130 which determines whether the patient falls asleep by executing a program that implements the flowchart described in FIG. 6. The processing may be a single program or may be executed as subroutine of other programs. Further, the control unit 100 may function as an activity amount calculating unit which calculates an amount of activity as the biological information.

A case where the system 1 in FIG. 2 is implemented by the detector 3 and the processor 5 in FIG. 1 will be described with reference to FIG. 4. The detector 3 includes a control unit 300, a biological signal acquiring unit 320 which is a sensor, a storage unit 330 and a communication unit 390.

Further, the control unit 300 includes a calculating unit 310 by executing software (programs) stored in the storage unit 330. The calculating unit 310 calculates a biological information on the basis of the biological signal acquired at the biological signal acquiring unit 320. Then, the calculated biological information is stored in biological information data 340, or transmitted to the processor 5 via the communication unit 390. Further, along with the biological information, the biological signal acquired at the biological signal acquiring unit 320 can be also transmitted to the processor 5 via the communication unit 390.

Regarding to a timing at which the biological information is transmitted from the detector 3 to the processor 5, and a timing at which the biological information is stored in the biological information data 340, the detector 3 may sequentially or periodically transmit the biological information to the processor 5.

The biological signal acquiring unit 320 corresponds to the acquiring unit 110 in FIG. 2, and the calculating unit 310 corresponds to the calculating unit 120 in FIG. 2. Further, the communication unit 390 is, for example, a communication interface which can be connected to a network (for example, a LAN/a WAN).

The processor 5 includes a control unit 500, a storage unit 530, an input unit 540, an output unit 550 and a communication unit 590. The processor 5 receives the biological information and the biological signal from the detector 3 via the communication unit 590. The received biological information is stored in biological information data 532.

The control unit 500 includes a determining unit 510 or a patient state acquiring unit 520 by executing software (programs) stored in the storage unit 530. The determining unit 510 determines the state of the patient P on the basis of the received biological information and biological signal. In a similar manner, the patient state acquiring unit 520 acquires a state of the patient which indicates whether the patient P is in the bed 10 on the basis of the received biological information and biological signal. The states of the patient are stored in patient state data 534.

Note that the determining unit 510 corresponds to the determining unit 130 in FIG. 2. The patient state acquiring unit 520 corresponds to the patient state acquiring unit 140 in FIG. 2. The input unit 540 corresponds to the input unit 160 in FIG. 2. The output unit 550 corresponds to the output unit 170 in FIG. 2. The storage unit 530 corresponds to the storage unit 150 in FIG. 2.

1.3. Processing Flow

The processing in the present embodiment will be described with reference to FIG. 5. First, the control unit 100 determines whether or not the patient goes to bed (step S102). For example, the patient state acquiring unit 140 determines that the patient P has gone to bed by detecting that the patient P is physically in the bed 10 or by detecting a state of the posture of the patient P indicative that the patient is going to bed (for example, that the patient is in a "recumbent position"), and determines that the patient has gone to bed as of the time of such detection.

Once the patient state acquiring unit 140 determines that the patient P has gone to bed, the control unit 100 changes the threshold stored in the storage unit 530 from a first threshold to a second threshold (step S104). The threshold is a threshold for determining whether the patient is in a "sleeping" state or in an "awake" state. In the present embodiment, in a default case, i.e., when the patient is sleeping, the threshold is set at the first threshold (value "1" in FIG. 3 for example corresponds to the first threshold), whereas, in the time period right after the detection that the patient has just gone to bed, during which time period the control unit 100 is making a determination as to whether the patient has fallen asleep, the threshold is the second threshold which is smaller than the first threshold. If the first threshold is set at "1" in FIG. 3 for example, the second threshold is preferably equal to or less than "0.5", and is "0.05" in the present embodiment.

Thus, immediately after the patient goes to bed, while the control unit 100 is determining whether the patient has fallen asleep, the control unit 100 is more likely to determine the patient's state as the "awake" state rather than the "sleeping" state because the second threshold, which is in effect during this time, is smaller than the first threshold which will be in effect during sleep.

This threshold setting is made so as to prevent the "awake" state from being erroneously determined as the "sleeping" state, because the patient during that period right after the determination of "goes to bed" usually does not move although the patient is still in the "awake" state. Therefore, the control unit 100 uses the second threshold during that period right after the determination of "goes to bed" up until the patient is determined to have fallen asleep.

Subsequently, the determining unit 130 (control unit 100) executes processing to determine whether the patient P is the "awake" state or the "sleeping" state (step S106). For example, the determining unit 130 determines the state of the patient on the basis of the amount of activity detected in a given certain time range.

For example, in the case where an amount of activity at a time point when the determining unit 130 makes the determination of whether the patient P is the "awake" state or the "sleeping" state (upon sleep determination) is $A_0$, an amount of activity one minute before is $A_{-1}$, and an amount of activity one minute later is $A_{+1}$, the determining unit 130 calculates: determination value $D=0.001\times(1.25\times A_{-4}+0.89\times A_{-3}+0.80\times A_{-2})+0.86\times A_{-1}+2.42\times A_0+1.26\times A_{+1}+1.20\times A_{+2})$ That is, the determining unit 130 determines a state of the patient at the time $A_0$ by utilizing an amount of activity $A_{-4}$ four minutes before, to an amount of activity $A_{+2}$ two minutes later.

Then, the determining unit 130 decides the state of the patient as the "awake" state if the determination value D is equal to or greater than the threshold (the first threshold or the second threshold depending on the time period as discussed above), and determines the state of the patient as the "sleeping" state if the determination value D is less than the threshold.

For example, in step S106, the second threshold "0.05" is set as the threshold, and the state of the patient is determined as the "awake" state if the determination value is equal to or greater than "0.05".

Subsequently, it is determined whether or not the patient has fallen asleep through processing described in FIG. 6 (step S108). Here, in the case where the patient P has not fallen asleep yet, the processing returns to step S106.

The processing in the step 108 in FIG. 5 will be described with reference to FIG. 6. The processing is processing for determining whether or not the patient has fallen asleep. While various kinds of definition of whether or not the patient has fallen asleep are used, most simply, the period which the patient has fallen asleep can be defined as a period between a time a light is turned off or the patient goes to bed and a time the state of patient is determined as a "sleeping" state for the first time.

Specifically, first, the state of the patient P is acquired (step S152). Subsequently, in the case where the state of the patient P is the "sleeping" state, it is determined that the patient has fallen asleep (step S154: Yes→step S156). Note that a result that the patient has fallen asleep may be reflected using, for example, a flag, or an attribute of a state of the patient may be provided.

Figure 5:
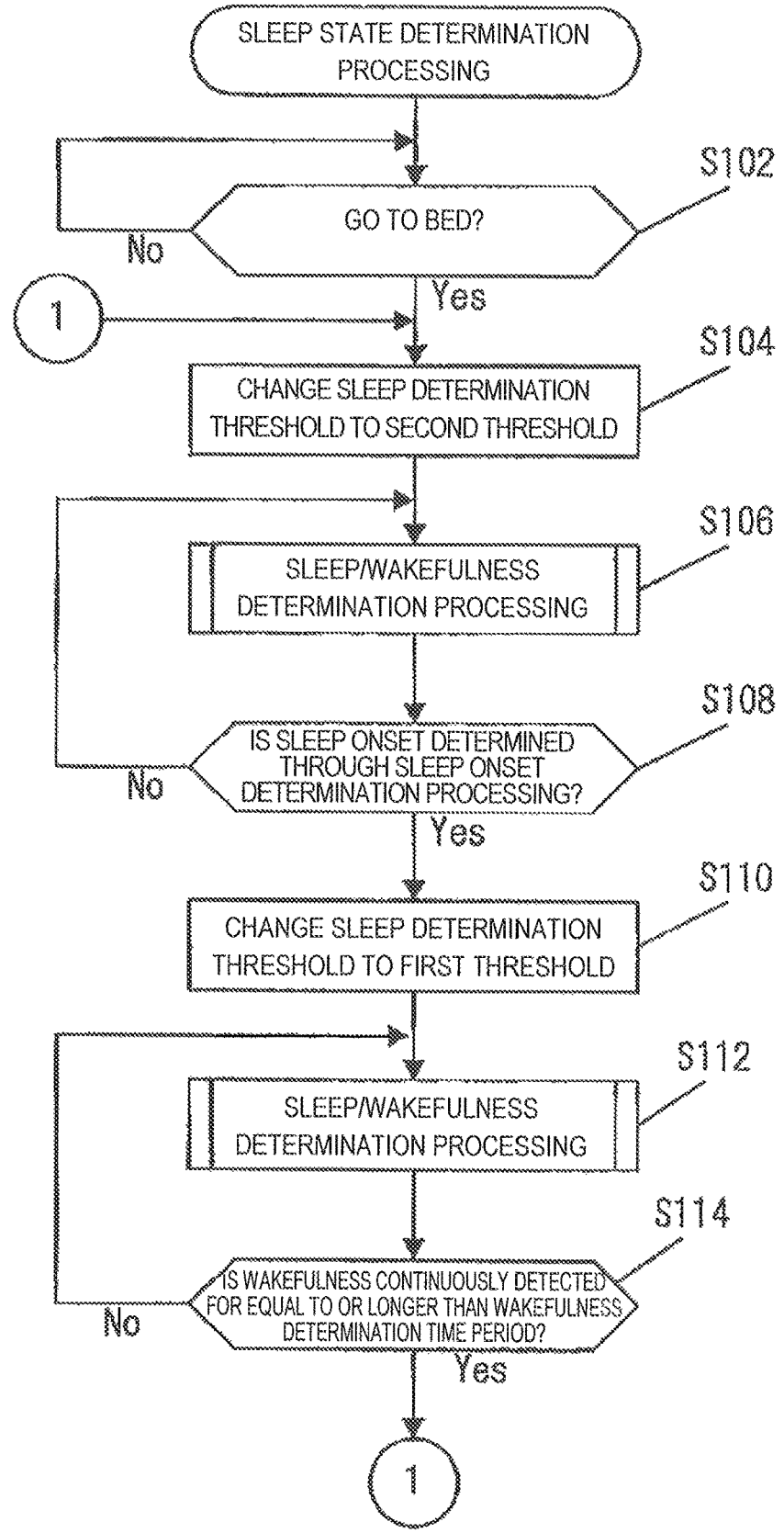
FIG. 5 is a flowchart for explaining processing how to evaluate state of a target person in the first embodiment.

Further, while, in the present embodiment, in the case where it is determined that the state of the patient is the "sleeping" state in step S108 in FIG. 5, the control unit 100 may simply determine that the patient has fallen asleep.

Further, while, in the case where it is determined that the state of patient is the "sleeping" state, it is determined that the patient has fallen asleep, it may be determined that the patient has fallen asleep in the case where the state of the patient is continuously determined as the "sleeping" state a plurality of times. For example, it may be determined that the patient has fallen asleep in the following cases.

(1) The control unit 100 may determine the patient has fallen asleep if the state is determined as the "sleeping" state for the first time under the condition that the "sleeping" state will continues for equal to or longer than a predetermined time period (for example, 3 minutes, 5 minutes, 10 minutes).

Further, in the case where the "sleeping" state is determined from the biological information in a stepwise manner including a plurality of stages, (2) The control unit 100 may determine the patient has fallen asleep if the state is determined as the "sleeping" state for the first time in at least one of stages. However, in the case where the stage of sleeping is stage 1, start of the stage 1 is determined as sleep onset under the condition that the stage continuously transitions to one of stage 2, stage 3 and REM.

(3) a period in which the state is determined as one of stages of sleeping for the first time is determined as sleep onset. However, in the case where the stage of sleeping is stage 1, start of the stage 1 is determined as sleep onset under the condition that the stage 1 or subsequent stage 2, stage 3 and REM continues for equal to or longer than a predetermined time period (for example, 3 minutes, 5 minutes, 10 minutes).

(4) a period in which the state is determined as one of stages of sleeping 2 and 3, and REM for the first time is determined as sleep onset.

(5) a period in which the state is determined as one of stages of sleeping 2 and 3, and REM for the first time is determined as sleep onset. However, start of the stage 2 is determined as sleep onset under the condition that the stage 2 or subsequent stage 3 and REM continues for equal to or longer than a predetermined time period (for example, 3 minutes, 5 minutes, 10 minutes).

Returning to the processing in FIG. 5, in the case where it is determined that the patient has fallen asleep (step S108: Yes), the threshold is changed from the second threshold to the first threshold (step S110). That is, because the patient has fallen asleep and the state of the patient P transitions to the "sleeping" state, the sleep determination threshold is changed to the first threshold which is greater than the second threshold. By this means, the determining unit 130 determines the state whether the patient P is "sleeping" or "awake" as usual.

The determining unit 130 executes the processing for determining the state whether the patient P is "sleeping" or "awake" (step S112). At this time, the threshold is set at the first threshold (for example, "1.0").

If the control unit 100 continuously detects that the patient P is "awake" for equal to or longer than the time period for determining whether the patient wakes up which is described in FIG. 3, the processing transitions back to the processing in step S104, and the control unit 100 executes the processing of step S104 which uses the second threshold as discussed above (step S114: Yes→step S104). For example, in a case of the present embodiment, the time period for determining whether the patient wakes up may be set at "6 minutes" in FIG. 3.

For example, the control unit 100 performs the processing of step S104 again in the case where the "awake" state is continuously detected as the state of the patient for "6 minutes" or in the case where the status of the patient P where the patient is not in the bed is continuously detected for "1 minute". By this means, it is possible to determine an appropriate the status of the patient P even after the patient has awakened after having been asleep.

Note that, If the control unit 100 doesn't continuously detect that the patient P is "awake" for equal to or longer than the time period for determining whether the patient wakes up which is described in FIG. 3, the determining unit 130 continuously executes the processing of step S112 which uses the first threshold as discussed above (step S114: No→step S112).

Further, in the case where the control unit 100 becomes unable to determine the state of the patient during the above-described processing (for example, the biological signal is no longer acquired, where the patient is not in the bed is detected, operation is cancelled by the patient/operator, or the like), the present processing may be finished.

[1.4. Effects of this Embodiment]

According to the present embodiment, it is possible to make setting so that the state of the patient when the patient starts falling asleep is less likely to be determined as the "sleeping" state than in other periods. By this means, it becomes possible to appropriately determine the state of the patient. Thus, immediately after the patient goes to bed, while the control unit 100 is determining whether the patient has fallen asleep, the control unit 100 is more likely to determine the patient's state as the "awake" state rather than the "sleeping" state because the second threshold, which is in effect during this time, is smaller than the first threshold which will be in effect during sleep.

Figure 7A:
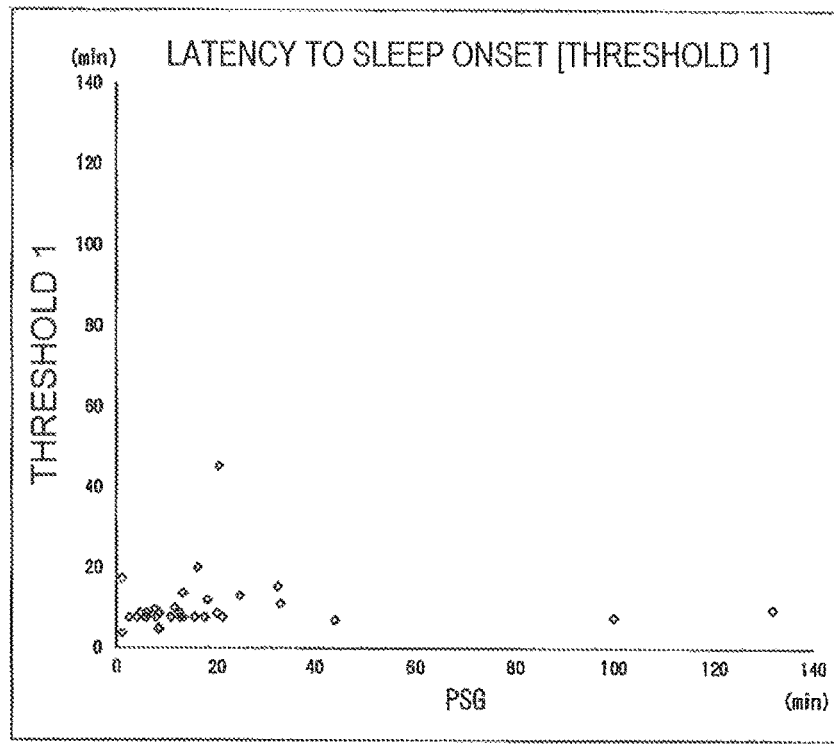
FIG. 7A to FIG. 7B are diagrams for explaining effects of the first embodiment.
Figure 7B:
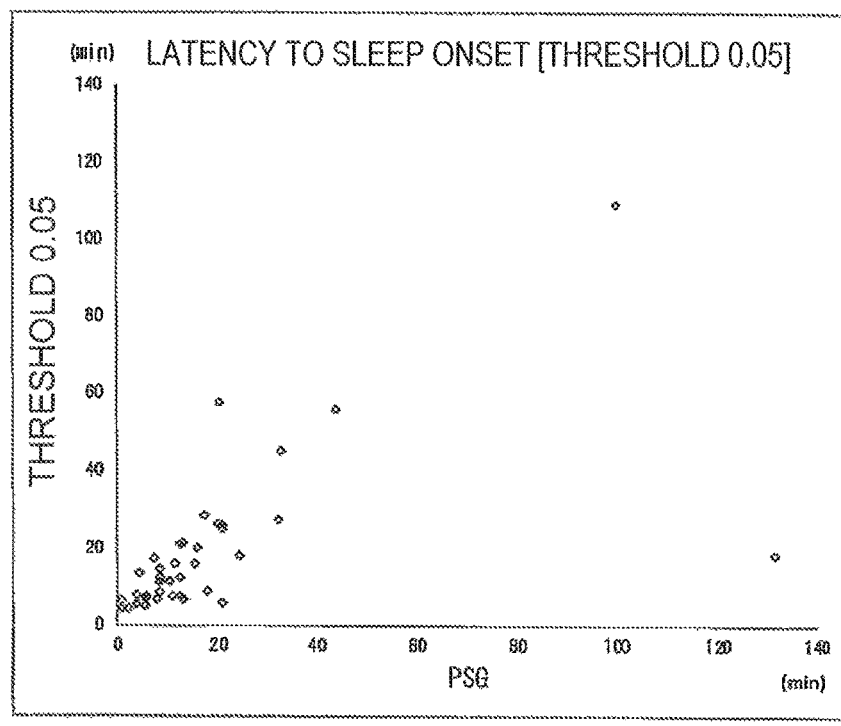

FIGS. 7A and 7B are graphs illustrating time periods until the patient is in the "sleeping" state (from the time when the patient goes to bed until the time when the patient is in the "sleeping" state). A horizontal axis indicates time periods (minutes) determined using PSG (polysomnogram), and a vertical axis indicates time periods (minutes) determined by a non-wearable apparatus utilizing the sensor described in the present embodiment.

FIG. 7A is a graph in the case where the threshold is set at "1", and FIG. 7B is a graph in the case where the threshold is set at "0.05".

In FIG. 7A, the values largely differ between time period determined by the case using the PSG and time period determined by the case using the non-wearable apparatus. That is, the time period determined by the non-wearable apparatus is shorter than the time period determined using the PSG, which means time period determined by the non-wearable apparatus is likely to be determined shorter than actual period that the patient starts falling asleep.

However, as illustrated in FIG. 7B, in the case where the threshold upon start of measurement (that is, immediately after the patient goes to bed) is set at "0.05", more favorable correlation can be obtained between the above two cases.

In this manner, by making setting so that the state of the patient when the patient starts falling asleep is less likely to be determined as the "sleeping" state than in other periods by changing the threshold for determining the state of the patient (the sleeping state or the awake state), it is possible to accurately determine the state of the patient P. In particular, in the case where it is determined whether the patient is easy to fall asleep or difficult to fall asleep, or quality of sleep is evaluated, it becomes possible to acquire a more accurate time period.

2. Second Embodiment

A second embodiment will be described in FIGS. 8 and 9. In the first embodiment, the control unit 100 determines the state of the patient using timings when the state of patient is determined as a "sleeping" state for the first time. In the present embodiment, an amount of activity is utilized for determining whether the patient has fallen asleep.

Figure 8:
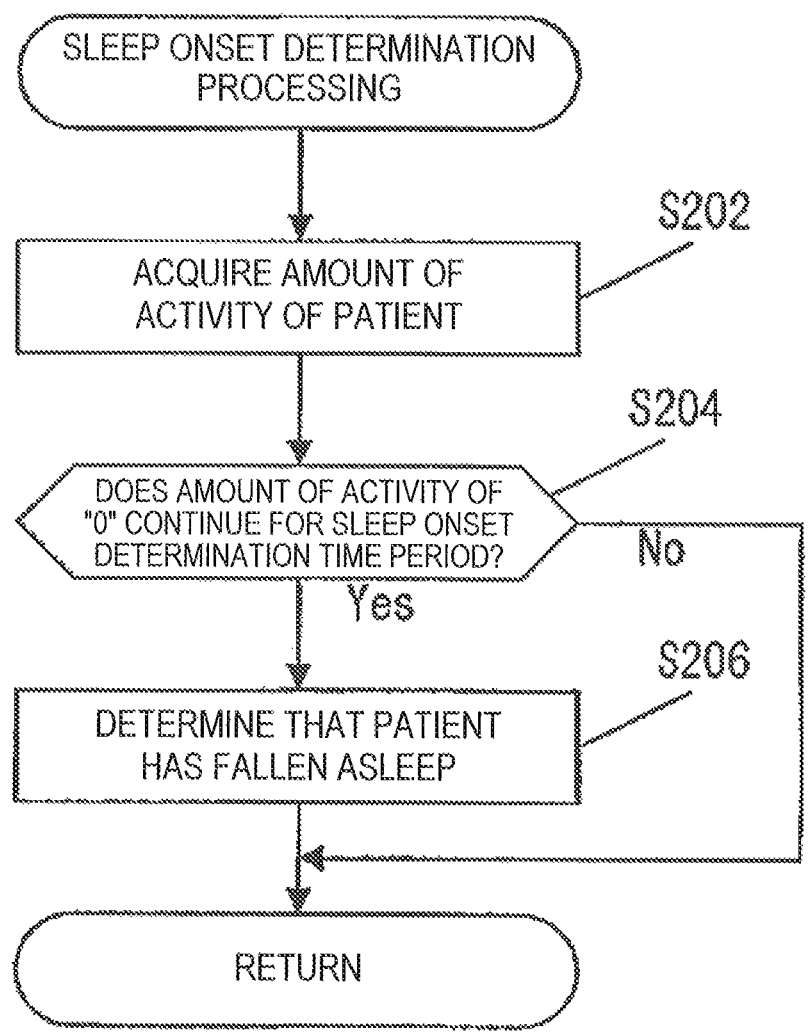
FIG. 8 is a flowchart for explaining processing whether the target person starts falling asleep or not in a second embodiment.

FIG. 8 shows a processing for determining whether or not the patient has fallen asleep of this embodiment. Other configuration and processing are the same as the first embodiment.

In the present embodiment, the determining unit 130 detects an amount of activity of the patient P (step S202). The determining unit 130 then determines that the patient has fallen asleep in the case where the amount of activity of substantially "0" continues for a time period for determining whether the patient wakes up (step S204: Yes).

Here, the time period is a time period in which it is determined that the patient has fallen asleep in the case where the activity amount is continuously substantially "0" (that is, while the activity amount is preferably "0", also including a case, for example, the activity amount is substantially "0"). The time for determining whether the patient wakes up is a value stored in the parameter table 156, and, while, in the present embodiment, the time period is set at "6 minutes", the time period only has to be a time period from "5 minutes" to "10 minutes".

Figure 9:
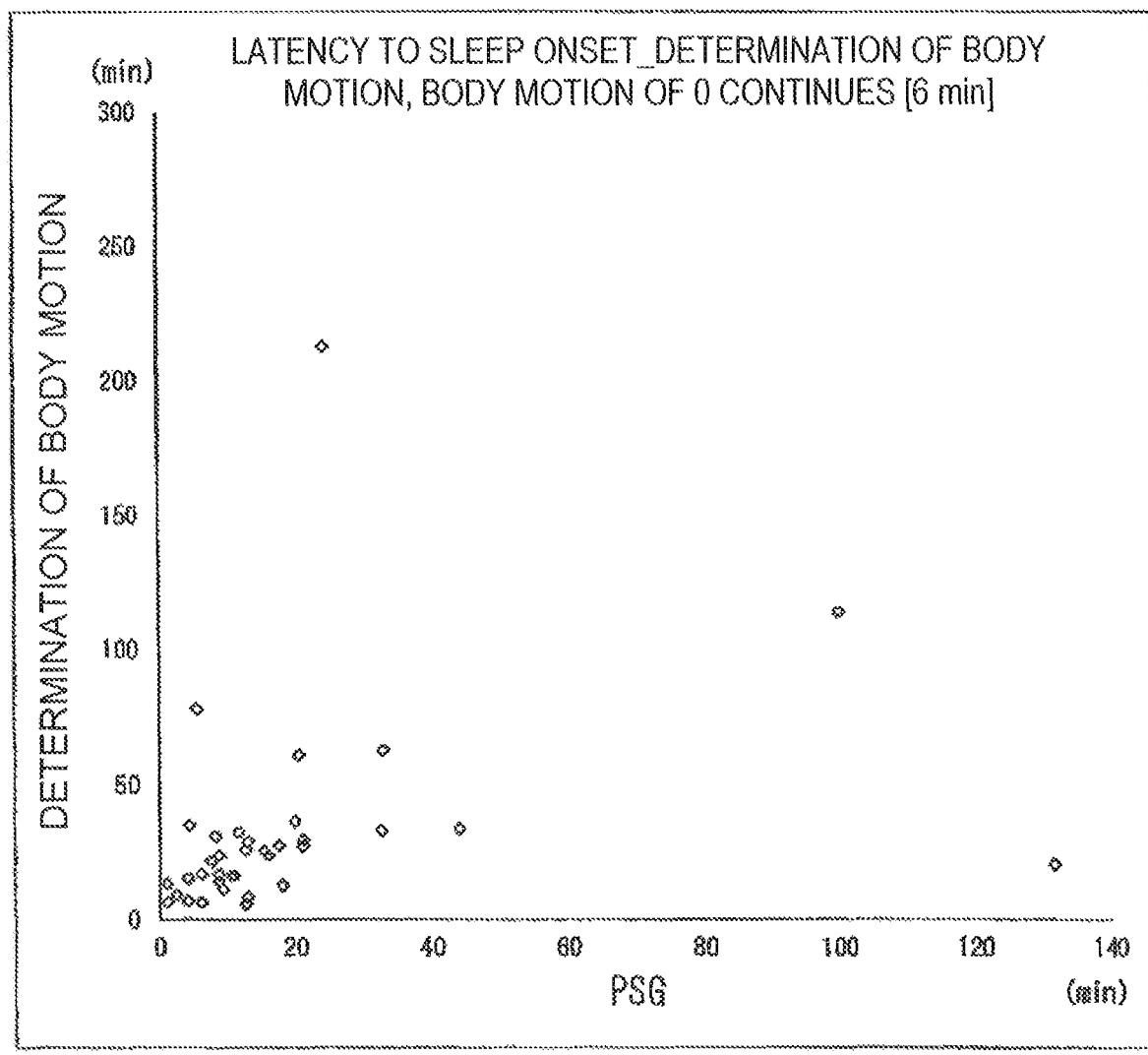
FIG. 9 is a diagram for explaining effects of the second embodiment.

FIG. 9 is a graph illustrating time period until the patient is in a "sleeping" state. A horizontal axis indicates the time period (minutes) determined by the PSG (polysomnogram), and a vertical axis indicates the time period (minutes) determined by a non-wearable apparatus which utilizes the sensor described in the present embodiment.

As illustrated in FIG. 9, there is a higher correlation between the time period using the PSG and the time period obtained by applying the present embodiment than that with the conventional method. Therefore, also in the present embodiment, it is possible to appropriately determine the state of the patient when the patient starts falling asleep.

Note that, the first embodiment and the second embodiment may be combined and applied. That is, two timings at which it is determined that the patient has fallen asleep in the first embodiment, and at which it is determined that the patient has fallen asleep in the second embodiment are obtained.

Then, an earlier timing at which it is determined that the patient has fallen asleep may be utilized as a timing at which the patient has fallen asleep, and processing of returning the threshold to the normal first threshold may be performed. Further, a state of the patient in a period from when determination is performed with the first threshold until when the state of the patient is determined as the sleeping state with the second threshold may be determined as a "transition state from awake to sleeping" separately from normal awake and sleeping states.

3. Third Embodiment

Figure 10:
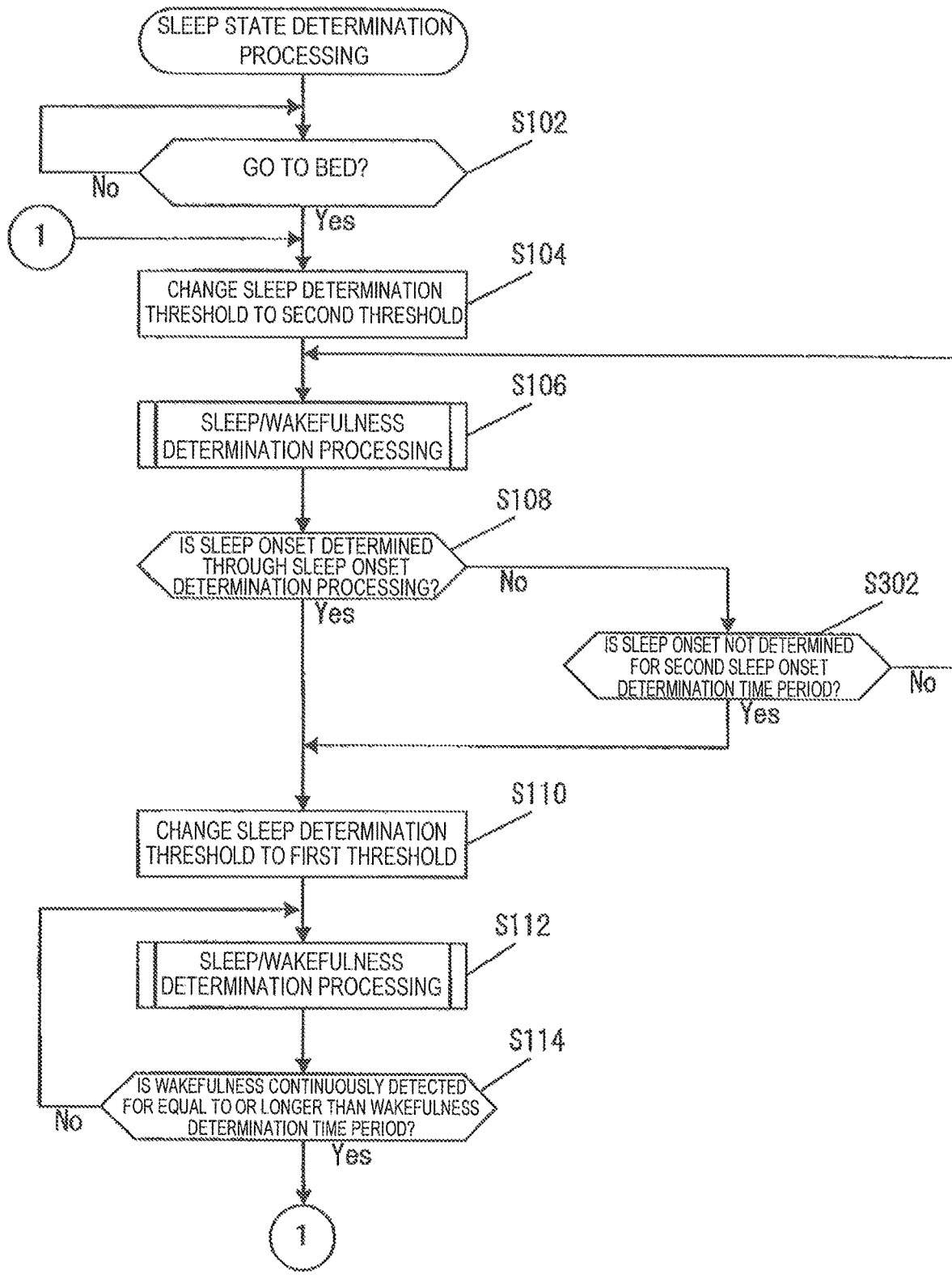
FIG. 10 is a flowchart for explaining processing how to evaluate state of the target person in a third embodiment.

A third embodiment will be described in FIG. 10. FIG. 10 shows a flowchart for explaining processing how to evaluate state of the patient in the second embodiment. The third embodiment is an embodiment in which the threshold is returned to the normal first threshold in the case where sleep onset of the patient is not determined in the processing of step S108.

The present embodiment will be described as an embodiment in which the processing in FIG. 5 in the first embodiment is replaced with the processing in FIG. 10. Note that this can similarly apply to the second embodiment.

In step S108, in the case where it is not determined that the patient has fallen asleep (step S108: No), the control unit 100 determines whether or not it is not determined that the patient has fallen asleep for a second time period (step S302). Here, the second time period is a threshold for a time period in which it is not determined that the patient has fallen asleep. The control unit 100 returns the threshold from the second threshold to the first threshold in the case where the second time period has elapsed.

In the case where it is not determined that the patient has fallen asleep for the second period, the control unit 100 changes the threshold to the first threshold (step S302: Yes→step S110). In the case where the second time period has elapsed since the patient goes to bed (awakens), normal processing of determining whether the patient is the sleeping state or the awake state.

The second time period is stored in the parameter table 156, and, while, in a case of the present embodiment, the second time period is, for example, set at "20 minutes", the second time period may be from "10 minutes" to "30 minutes". Note that, as the second time period, for example, a maximum value or an average time period of subjective time period to sleep onset of the patient may be stored, or the second time period may be changed in accordance with a disease condition. For example, in a case of insomnia or depression, because the patient little moves upon sleep onset and the state is likely to be determined as the "sleeping" state, so that time period to sleep onset is underestimated, it can be considered that the second time period is set longer. Further, in the case where involuntary movement continuously occurs during sleeping, in the present embodiment, the state is scarcely determined as the "sleeping" state. By changing the threshold to the first threshold which is a normal threshold after the second time period has elapsed, it is possible to prevent overestimation during latency to sleep onset.

4. Fourth Embodiment

A fourth embodiment will be described in FIG. 11. The fourth embodiment is an embodiment in which, in the case where sleep onset of the patient is not determined in the processing step S108, conditions, or the like, for determining sleep onset are changed by changing each parameter.

The present embodiment will be described as an embodiment in which the processing in FIG. 10 in the third embodiment is replaced with processing in FIG. 11. Note that this can similarly apply to other embodiments.

In the case where it is not determined that the patient has fallen asleep through the processing step S108, when the second time period has not elapsed, each parameter value is changed (step S302: No→step S402). Note that, in the case where this processing is applied to FIG. 5 in the first embodiment, the step S302 becomes unnecessary. Here, as a method for changing parameter values, there can be the following methods.

(1) The period for determining whether patient has fallen asleep is shortened. For example, the time period is changed from "6 minutes" to "3 minutes".
(2) The threshold for determining whether the patient falls asleep is changed. For example, the threshold is changed from "0.05" to "0.1". That is, the threshold is changed to a third threshold which is smaller than the first threshold and which is greater than the second threshold.
(3) The threshold is changed in a stepwise manner. For example, the threshold is changed to "0.25" when 15 minutes have elapsed since the patient goes to bed, changed to "0.5" when 30 minutes have elapsed since the patient goes to bed, changed to "0.75" when 45 minutes have elapsed since the patient goes to bed, and changed to "1" when one hour has elapsed since the patient goes to bed. That is, a stepwise threshold is utilized as the third threshold.

Further, these parameter values may be changed for each patient. For example, the parameter values may be determined on the basis of history of disease, age, time, and a sleep state until time for bed.

By changing the parameter values in this manner, it becomes possible to more appropriately determine the state of the patient. For example, there should be a time slot during which the patient can easily fall asleep in accordance with time, and the time slot should change continuously to some extent. Changing the threshold in a stepwise manner enables determination close to actual sleep for each patient.

5. Fifth Embodiment

Figure 12:
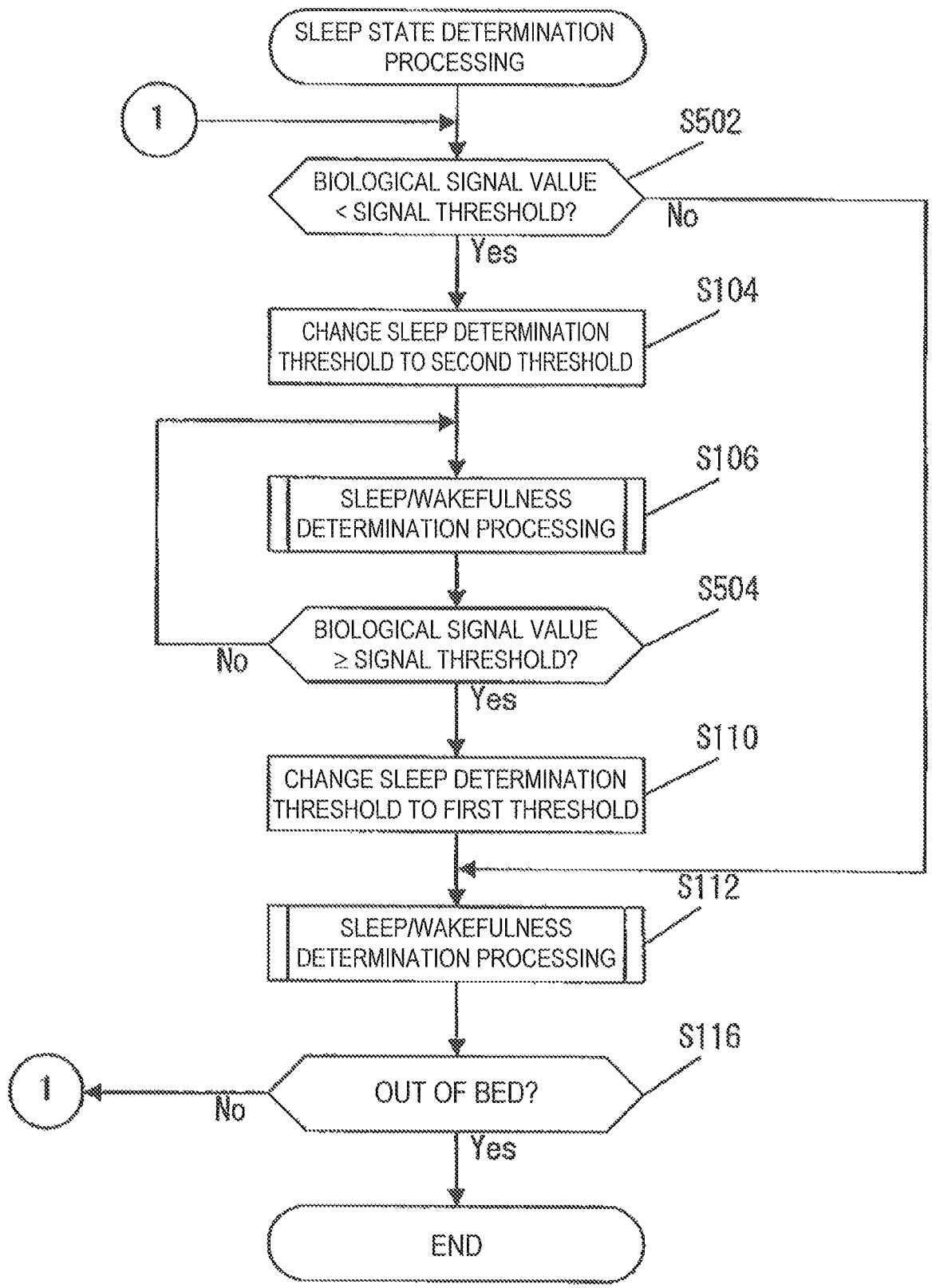
FIG. 12 is a flowchart for explaining processing how to evaluate state of a target person in a fifth embodiment.

A fifth embodiment will be described in FIG. 12. In the above-described embodiments, determination of the sleep state in the sleep onset period has been described. Because the patient does not move in the sleep onset period, and the state is likely to be determined as the sleeping state, setting is made so that the state is determined as awake by changing the threshold.

In the present embodiment, a case where input to the sensor is small will be described as an environment where the state of the patient is likely to be determined as sleeping. This case tends to occur, for example, in the case where the patient is in a seated position or sitting square on the bed, or in the case where the patient is located away from the sensor on the bed.

That is, conventionally, in the case where a biological signal of the patient is acquired, and the state of the patient is determined, if the biological signal cannot be correctly acquired because the acquired biological signal is weak, there is a trouble that the state of the patient cannot be appropriately determined. The present embodiment can solves the trouble.

The present embodiment will be described as an embodiment in which the processing in FIG. 5 in the first embodiment is replaced with the processing in FIG. 12. Note that this can similarly apply to other embodiments.

First, it is determined whether or not a biological signal value (signal strength) when the patient is at rest, acquired by the acquiring unit 110 is less than a predetermined signal threshold (step S502). Here, if the biological signal value is equal to or greater than the predetermined signal threshold, the processing step S112 is executed (step S502: No→step S112). Note that, in the case where a largest biological signal value detected by the biological signal acquiring unit when the patient is at rest is respiratory movement, signal strength in a frequency domain corresponding to the respiratory movement is used for comparison with the signal threshold.

In the case where the biological signal value is less than the predetermined signal threshold, the threshold is changed to the second threshold (step S502: Yes→step S104). Then, the processing step S106 is executed, and, in the case where the biological signal value (signal strength) becomes equal to or greater than the signal threshold, the threshold is changed to the first threshold (step S106→step S504: Yes→step S110).

According to the present embodiment, if the biological signal value (signal strength of the biological signal) is equal to or greater than the predetermined signal threshold, the processing step S112 is executed with the normal threshold. In the case where the biological signal value is less than the predetermined signal threshold, the threshold is changed to a threshold with which the state of the patient is less likely to be determined as the sleeping state.

6. Sixth Embodiment

A sixth embodiment will be described. The sixth embodiment is an embodiment in which a plurality of thresholds for determining whether the patient falls asleep can be set in accordance with a sleep environment, or the like, of the patient.

For example, in step S104 in FIG. 5, the threshold is changed to the second threshold. At this time, there are provided a plurality of values (parameters) to be set as the second threshold, and a value to be set may be changed in accordance with determination conditions such as, for example, time for bed and a state of the patient (for example, the patient has lack of sleep, has got a nap, has drank alcohol, or the like).

For example, while it should be difficult for the patient to sleep during the day compared to during the night, there is also a case where the state of the patient is likely to be determined as sleeping during the day because there is tendency that a low amount of activity is calculated during the day, such as in the case where a low amount of activity is calculated because the patient watches TV or reads a book and in the case where detection sensitivity of body motion in a seated position which is common as a state of the patient during the day is low depending on types of the detection apparatus. In such cases, it becomes possible to perform appropriate determination by setting a low threshold (a threshold with which the state is less likely to be determined as sleeping) during the day and setting a high threshold (a threshold with which the state is likely to be determined as sleeping) during the night so that the threshold is set on the basis of determination conditions such as biological rhythm, a sleep tendency curve and rhythm within a day of activity amount detection sensitivity.

Figure 11:
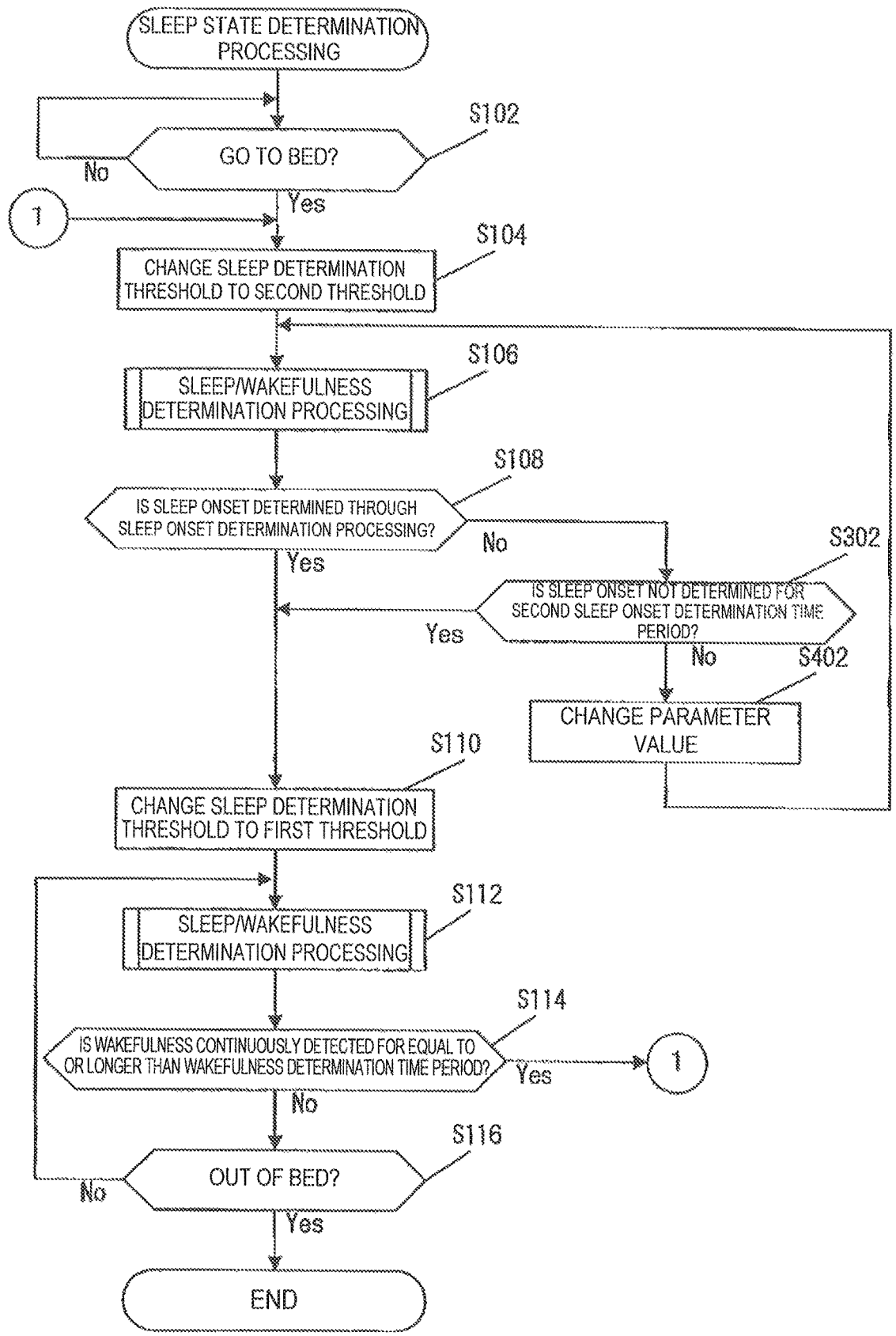
FIG. 11 is a flowchart for explaining processing how to evaluate state of a target person in a fourth embodiment.

Further, in the case where the present embodiment is combined with FIG. 11, it is possible to further change the parameter values in a stepwise manner. By this means, it becomes possible to perform more appropriate determination.

7. Modified Example

While the embodiments of the present invention have been described in detail above with reference to the drawings, a specific configuration is not limited to these embodiments, and design, or the like, which are within the scope not deviating from the gist of the present invention are included in the claims.

Further, while, in the present embodiment, the biological information is output from the processor 5 on the basis of the result output from the detector 3, the detector 3 may perform all calculation. Further, as well as a configuration where application is installed and implemented at a terminal apparatus (for example, a smartphone, a tablet and a computer), it is, for example, also possible to perform processing on the server side and return the processing result to the terminal apparatus.

For example, the above-described processing may be executed on the server side by the biological information being uploaded to the server from the detector 3. The detector 3 may be implemented by an apparatus such as a smartphone in which, for example, an acceleration sensor and a vibration sensor are incorporated.

Further, a program running at each apparatus in the present embodiment is a program of controlling a CPU, or the like, (a program for causing a computer to function) to execute the functions of the above-described embodiments. Information handled at these apparatuses is temporarily accumulated in a temporal storage apparatus (for example, a RAM) upon the processing, and, then, stored in a storage apparatus such as various kinds of ROMs, HDDs and SSDs, and read out, corrected and written by the CPU as necessary.

Further, in the case where the program is distributed to the market, it is possible to distribute the program stored in a portable recording medium, or forward the program to a server computer connected via a network such as the Internet. In this case, the storage apparatus of the server computer is, of course, also included in the present invention.

What is claimed is:

1. An evaluating apparatus comprising:
a sheet shaped sensor placed between a bottom frame of a bed and a mattress, the sensor configured to acquire a biological signal of a user; and
a controller configured to:
calculate an amount of activity of the user from the biological signal,
calculate a determination value from the amount of activity during a predetermined period of time,
compare the determination value to a threshold value to determine a state of the user as an awake state if the determination value is equal to or greater than the threshold value, and determine the state of the user as a sleeping state if the determination value is less than the threshold value,
wherein the threshold value is either a low threshold or a high threshold, the low threshold being lower than the high threshold,
in a period of time in which it has been determined that the user has not fallen asleep, by comparing the determination value with the low threshold, determine whether or not the user falls asleep,
during a period of time after it has been determined that the user has fallen asleep, by comparing the determination value with the high threshold, determine whether the user remains sleeping;
an output that outputs a sleeping state of the user based on the comparisons of the determination value with each of the low and high thresholds; and
a storage that stores the sleeping state of the user.

2. The evaluating apparatus according to claim 1, further comprising:
a further detector configured to detect a physical presence of the user in a bed or to detect that the user is in a recumbent position;
wherein the controller determines that the user has not fallen asleep by comparing the determination value with the low threshold upon detection by the further detector;
wherein, upon a determination that the user has fallen asleep by comparing the determination value with the low threshold, the controller determines whether the user remains sleeping by comparing the determination value with the high threshold in the period of time after it has been determined that the user has fallen asleep.

3. The evaluating apparatus according to claim 1, wherein the controller determines whether or not the user is sleeping by comparing the determination value with the high threshold when a strength of the biological signal detected by the detector is more than a predetermined threshold, and determines whether or not the user is sleeping by comparing the determination value with the low threshold when a strength of the biological signal detected by the detector is less than the predetermined threshold.

4. The evaluating apparatus according to claim 1, wherein the controller determines whether or not the user is sleeping by comparing the determination value with the high threshold during a daytime, and determines whether or not the user is sleeping by comparing the determination value with the low threshold during a night.

5. The evaluating apparatus according to claim 1, wherein the controller calculates the determination value from the amount of activity of the user during the predetermined period before a time point of determining that the user has fallen asleep and from the amount of activity of the user during a predetermined period after the time point of determining that the user has fallen asleep.

6. The evaluating apparatus according to claim 1, wherein the controller, after it is detected that the user has left the bed for a predetermined period of time, determines whether or not the user falls asleep after the period of time in which it has been determined that the user has not fallen asleep by comparing the determined value with the low threshold.

7. The evaluating apparatus according to claim 1, wherein the controller, if it is not determined that the user has fallen asleep for a predetermined period of time, changes the threshold value to a value greater than the low threshold and lower than the high threshold.

8. A non-transitory computer readable medium having stored thereon a program for causing a microprocessor to execute at least the following:
   acquiring a biological signal of a user from a sheet shaped sensor placed between a bottom frame of a bed and a mattress;
   calculating an amount of activity of the user from the biological signal;
   calculating a determination value from the amount of activity during a predetermined period of time;
   comparing the determination value to a threshold value to determine a state of the user as an awake state if the determination value is equal to or greater than the threshold value, and determining the state of the user as a sleeping state if the determination value is less than the threshold value,
   wherein the threshold value is either a low threshold or a high threshold, the low threshold being lower than the high threshold,
   in a period of time in which it has been determined that the user has not fallen asleep, by comparing the determination value with the low threshold, determining whether or not the user falls asleep;
   during a period of time after it has been determined that the user has fallen asleep, by comparing the determination value with the high threshold, determine whether the user remains sleeping;
   outputting a sleeping state of the user based on the comparisons of the determination value with each of the low and high thresholds; and
   storing the sleeping state of the user in the non-transitory computer readable medium.

9. The non-transitory computer readable medium according to claim 8, wherein the program is further for causing the microprocessor to execute, after it is detected that the user has left the bed for a predetermined period of time, a determination of whether or not the user falls asleep after the period of time in which it has been determined that the user has not fallen asleep by comparing the determined value with the low threshold.

10. The non-transitory computer readable medium according to claim 8, wherein the program is further for causing the microprocessor to execute, if it is not determined that the user has fallen asleep for a predetermined period of time, changing the threshold value to a value greater than the low threshold and lower than the high threshold.

* * * * *